US008121371B2

(12) United States Patent
Dewaele

(10) Patent No.: US 8,121,371 B2
(45) Date of Patent: Feb. 21, 2012

(54) METHOD OF PERFORMING MEASUREMENTS ON DIGITAL IMAGES

(75) Inventor: Piet Dewaele, Sint-Niklaas (BE)

(73) Assignee: Agfa Healthcare, Mortsel (BE)

( * ) Notice: Subject to any disclaimer, the term of this patent is extended or adjusted under 35 U.S.C. 154(b) by 0 days.

(21) Appl. No.: 13/163,470

(22) Filed: Jun. 17, 2011

(65) Prior Publication Data

US 2011/0249876 A1  Oct. 13, 2011

Related U.S. Application Data

(62) Division of application No. 11/265,307, filed on Nov. 2, 2005, now Pat. No. 8,014,625.

(60) Provisional application No. 60/631,664, filed on Nov. 30, 2004.

(30) Foreign Application Priority Data

Nov. 10, 2004 (EP) .................... 04105652

(51) Int. Cl.
  *G06K 9/00* (2006.01)
(52) U.S. Cl. .............. 382/128; 348/580; 345/629
(58) Field of Classification Search .............. 382/100, 382/128, 129, 130, 131, 132, 276, 277, 294, 382/293, 295, 296; 348/580; 345/619–689
See application file for complete search history.

(56) References Cited

U.S. PATENT DOCUMENTS

| 5,384,862 | A | | 1/1995 | Echerer et al. |
| 5,611,033 | A | * | 3/1997 | Pitteloud et al. .............. 345/629 |
| 5,740,267 | A | | 4/1998 | Echerer et al. |
| 5,850,836 | A | * | 12/1998 | Steiger et al. ............ 600/300 |
| 6,002,959 | A | * | 12/1999 | Steiger et al. ............ 600/425 |
| 2006/0029291 | A1 | | 2/2006 | Sun et al. |
| 2008/0123922 | A1 | * | 5/2008 | Gielen et al. ............ 382/131 |
| 2009/0290771 | A1 | * | 11/2009 | Frank et al. ............ 382/128 |

FOREIGN PATENT DOCUMENTS

| EP | 0 527 525 A2 | 2/1993 |
| EP | 0 610 605 A1 | 8/1994 |
| EP | 0 887 769 A1 | 12/1998 |
| EP | 1 349 098 A1 | 10/2003 |

OTHER PUBLICATIONS

European Patent Office, European Search Report in European Patent Application 04 10 5652 (Mar. 23, 2005).
Benameur et al., "3D/2D Registration and Segmentation of Scoliotic Vertebrae Using Statistical Models," 27(5): 321-337 (2003).
Brown, "A Survey of Image Registration Techniques," 24(2): 325-376 (1992).
Maintz et al., "A Survey of Medical Image Registration," 2(1): 1-37 (1998).
Penning et al., "Measurement of Angular and Linear Segmental Lumbar Spine Flexion-Extension Motion by Means of Image Registration," 14(2): 163-170 (2004).

* cited by examiner

*Primary Examiner* — Anand Bhatnagar
(74) *Attorney, Agent, or Firm* — Leydig, Voit & Mayer, Ltd.

(57) ABSTRACT

A first and a second image are expressed in a common coordinate system by applying a geometric transformation to the second image so as to map a structure in the second image onto a corresponding structure in the first image in a common coordinate system. Starting from initial values, the parameters of the geometric transformation are updated taking into account the result of an evaluation of a cost function.
Measurements are performed in the common coordinate system.

2 Claims, 6 Drawing Sheets

METHOD OF PERFORMING MEASUREMENTS ON DIGITAL IMAGES

CROSS-REFERENCE TO RELATED PATENT APPLICATIONS

This application is a divisional of U.S. patent application Ser. No. 11/265,307, filed Nov. 2, 2005, now U.S. Pat. No. 8,014,625, which claims priority to European Patent Application No. 04105652.4, filed Nov. 10, 2004, and U.S. Provisional Application 60/631,664, filed Nov. 30, 2004, each of which is incorporated herein in its entirety.

FIELD OF THE INVENTION

The present invention relates to a computer assisted method to perform measurements on digital radiographic images.

BACKGROUND OF THE INVENTION

A recurrent problem in radiological practice is the adjustment of two images to compare them, or to measure, calculate and visualize their difference in marked regions.

Typical radiological examinations are those of the vertebrae of the spine on radiographic images, or images of the stomach and blood vessels.

The differences introduced by patient positions, biomechanical motions such as flexion and extension, or exposure viewpoint make simple superimposition of two images not straightforward.

In the prior film-based art, superposition of two film images is achieved by superimposing one film onto another, whilst at the same time sliding the second film relative to the first one by successive translations and rotations such that the corresponding anatomic structures of interest geometrically match to each other. This operation is typically performed when both superimposed images are displayed on a lightbox, or alternatively positioned in front of a light intensive lamp. The resulting image that the radiologist examines is a combination of densities registered on both films in the regions where both films overlap, and equals the original film density in all other areas where only a single sheet is present.

The drawbacks of the film-based prior art can be summarized as follows.

It is difficult to correctly match by visual inspection structures that mutually correspond.

The act of superimposing the images must be repeated every time the images are to be matched, or when a sequence of structures of interest has to be matched. The manual procedure is thus fatiguing and error-prone.

Additional operations on the superimposed film combination, such as geometric measurements (distances, angles), are difficult to effectuate.

The film-based superimposition cannot be archived for further referral.

Different structures recorded on a single film cannot be registered with one another.

It is an aspect of this invention to provide a method to perform measurements on digital images that overcomes the drawbacks of the prior art.

Other aspects of the present invention will become apparent from the description given below.

SUMMARY OF THE INVENTION

The above aspects are realized by a method of performing measurements as set out in the appending claims.

The method of the present invention comprises the following steps:
(1) obtaining a digital signal representation of an image A,
(2) obtaining a digital signal representation of a reference image B,
(3) applying at least said digital signal representation of image A to a display device coupled to a computer and displaying image A,
(4) applying a geometric transform to image B so as to map at least a geometric structure in image B onto a corresponding geometric structure in image A in a common coordinate system,
(5) displaying transformed image B,
(6) performing a measurement in said common coordinate system using image A and transformed image B.

In one embodiment (i) initial parameters of said geometric transform are set. Next, (ii) the geometric transform with the set parameters is applied to image B so as to transform image B into a common coordinate system as image A. Then, (iii) a cost function is evaluated to generate a cost value indicative of a degree of alignment of the transformed image and image A and (iv) parameters of the geometric transform are updated taking into account said cost value. Steps (ii) to (iv) are re-iterated to obtain final parameters of said geometric transform when the generated cost value is optimal. The transform with these final parameters is applied to image B.

The images that considered may for example be images of the same patient taken at different moments in time or images of the same patient taken in different positions.

Alternatively the images may be an image of a patient and a reference image. Different types of images may be envisaged.

In a specific embodiment according to the present invention the images are additionally blended (also called 'fused'). In addition to the steps relating to image superposition as set out in claim 1, a blended image may be generated whereby each pixel value of the blended image is a combination of a corresponding pixel value in the first image and a corresponding pixel value in a transformed image resulting from applying the transform set out in claim 1.

Another aspect of the present invention relates to a method of determining an extent by which the position of a structure in a second image is rotated relative to its position in a first image as set out in the appending claims.

Still another aspect of this invention relates to methods of computing the angle of Cobb and the Ferguson angle.

Still another aspect relates to a method of identifying a vertebra in a spine image.

The embodiments of the methods of the present invention are generally implemented in the form of a computer program product adapted to carry out the method steps of the present invention when run on a computer. The computer program product is commonly stored in a computer readable carrier medium such as a CD-ROM.

Alternatively the computer program product takes the form of an electric signal and can be communicated to a user through electronic communication.

The current invention is particularly suited in the field of orthopedics and traumatology where cervical spine stability is analyzed by means of medical images and geometric measurements. Roentgenographical features that are checked in spinal injuries are the interspinous distance, the atlanto-axial relationship, the posterior axial line, the anteroposterior displacement and the angular displacement. These measurements are typically studied on lateral cervical spine radiographs in different positions of the spine (neutral, flexion and extension, active flexion and active extension, hyper-flexion and hyper-extension).

Angular displacement, for example, is measured at each vertebral level by superimposing the lateral view in hyperextension on the view in hyper-flexion by matching up the vertebral body on both X-ray films. In the technique of the prior film-based art, a line is drawn on the X-ray film in hyper-flexion parallel to the edge of the X-ray film in hyper-extension. This technique is repeated for each superior vertebra. The angles between successive lines are then measured. They represent the angular mobility of the cervical spine and are used to infer possible spinal injury.

The present invention is also suitable in a method as disclosed in European patent application EP 1 349 098 A1. This patent application discloses a method to perform measurements in digitally acquired medical images by grouping measurement objects and entities into a computerized measurement scheme consisting of a bi-directionally linked external graphical model and an internal informatics model.

In a measurement session according to European patent application 1 349 098 A1, a measurement scheme is retrieved from the computer and activated. Measurements are subsequently performed on the displayed image under guidance of the activated measurement scheme.

In this computerized method, a multitude of geometric objects are mapped in the digital image onto which other measurement objects and finally measurement entities (such as distances and angles) are based. The basic geometric objects are typically key user points, which define other geometric objects onto which geometric measurements are based. For example, two pairs of key points each define a line, and an angle between the resulting line pair, representing the angulation between anatomic structures, is computed.

Specific and preferred embodiments of the present invention will be described below with reference to the following drawings.

DETAILED DESCRIPTION OF THE INVENTION

Figure 1:
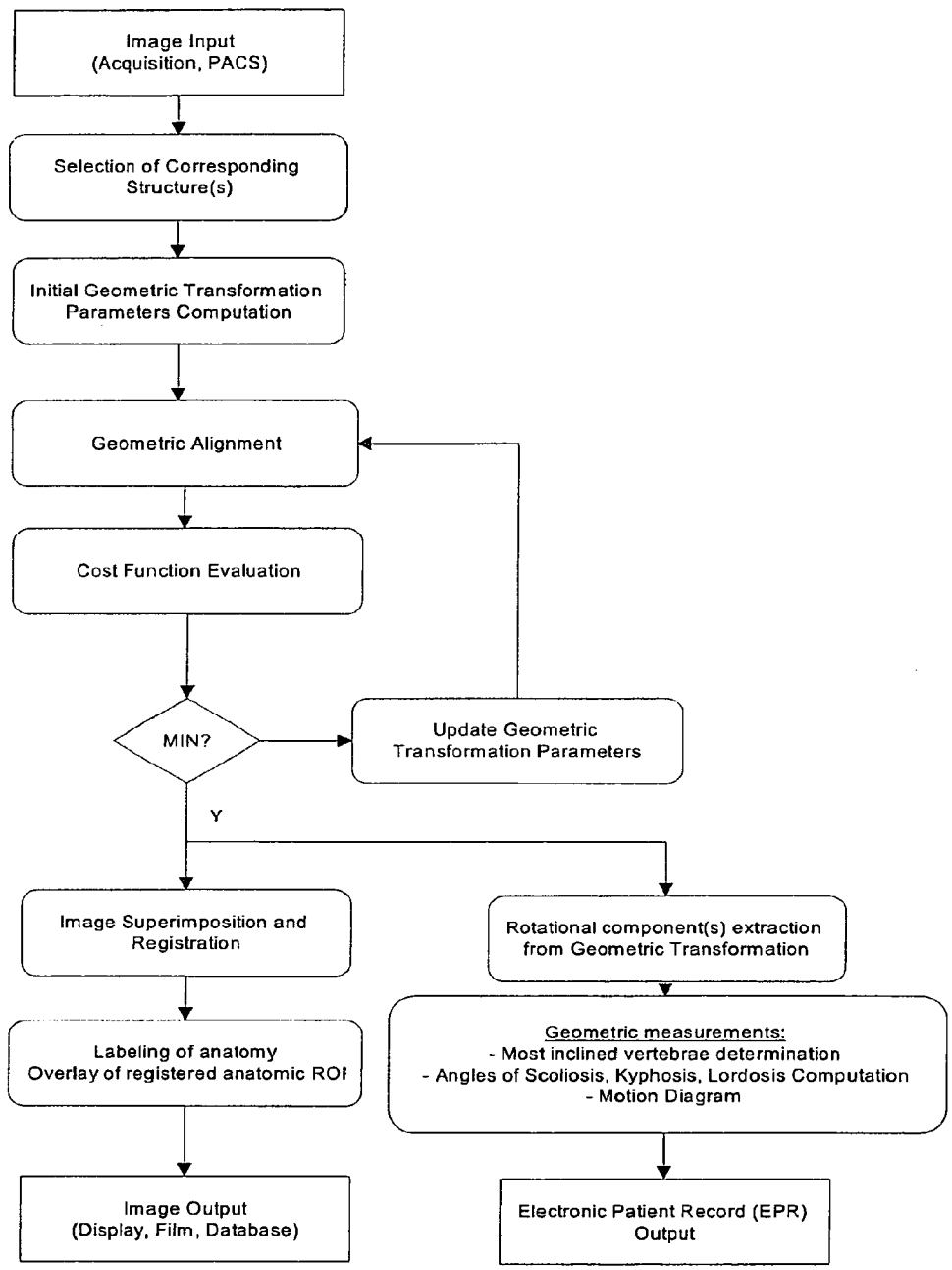
FIG. 1 illustrates an aspect of the present invention.
Figure 2:
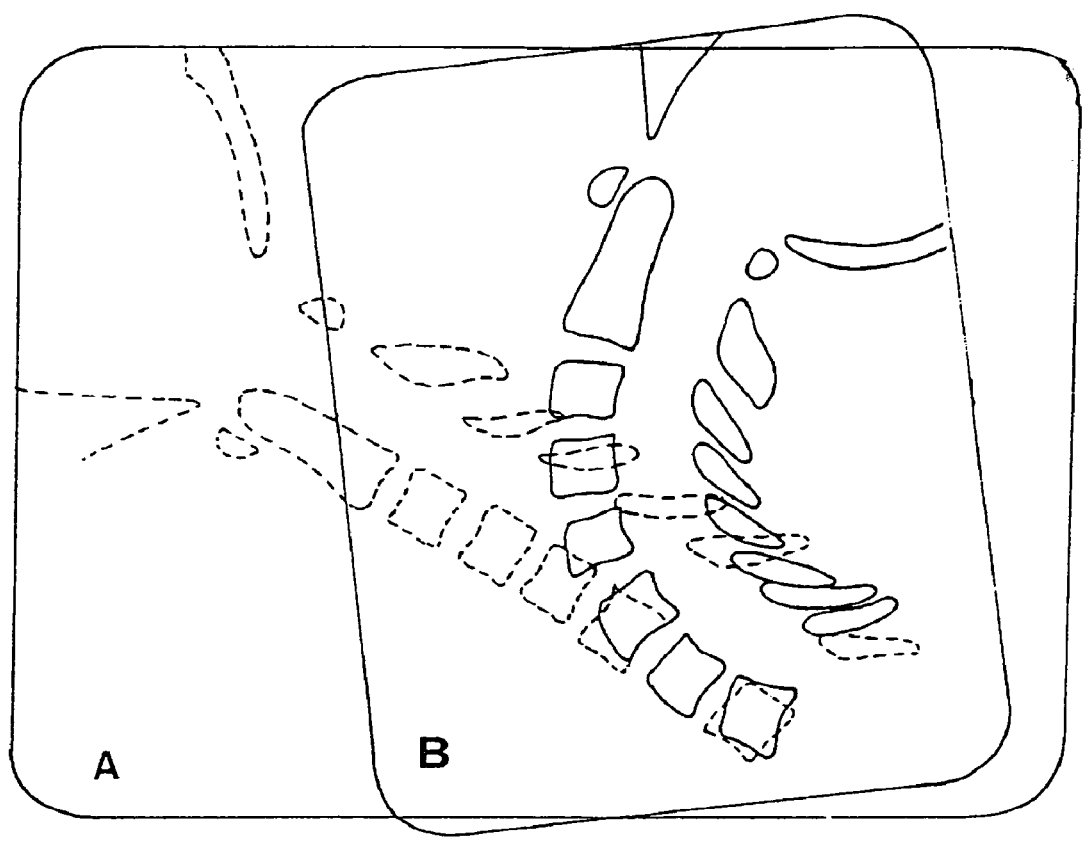
FIG. 2 shows an image B (extension lateral cervical spine radiograph) registered and superimposed on an image A (flexion lateral cervical spine radiograph)
Figure 3:
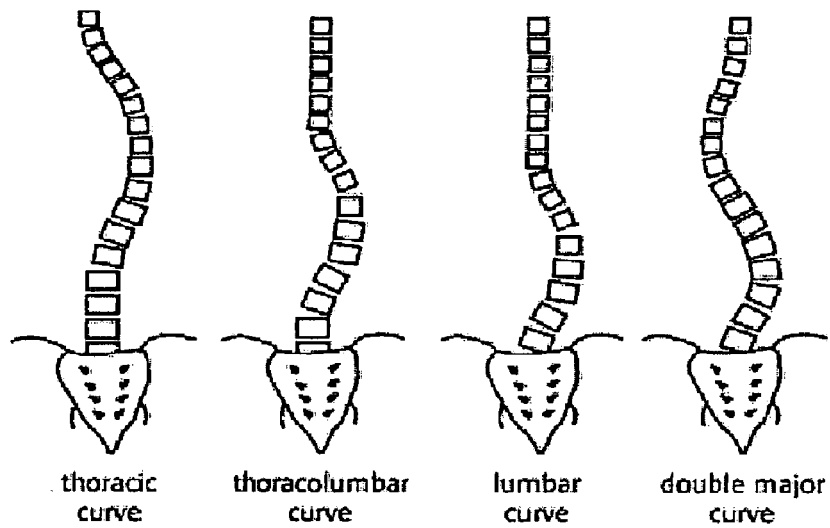
FIG. 3 shows a description of scoliosis as to the location of the curve in the frontal full-spine radiograph.
Figure 6:
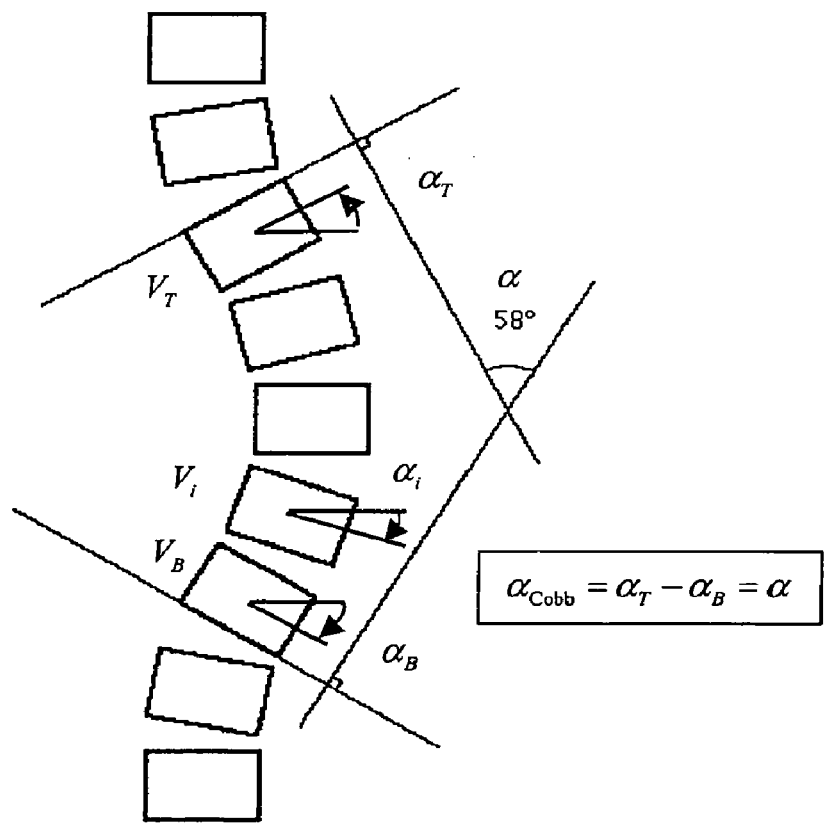
FIG. 6 shows the computation of the angle of Cobb according to the present invention. The angle $\alpha_i$ of each vertebra $V_i$ with respect to a horizontal reference axis is determined by calculating the rotational component of a registration of a model vertebra (retrieved either e.g. from a model image mask of the vertebra of the same name, a vertebra of same name on a previous image of the same patient, or a upwardly or downwardly located vertebra of the same image)
Figure 4:
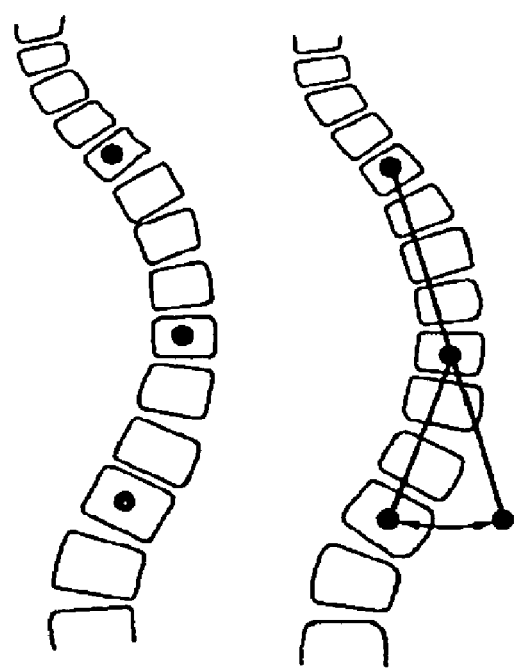
FIG. 4 shows the method of Ferguson for measurement of the angle of scoliosis in the frontal full-spine radiograph.
Figure 5:
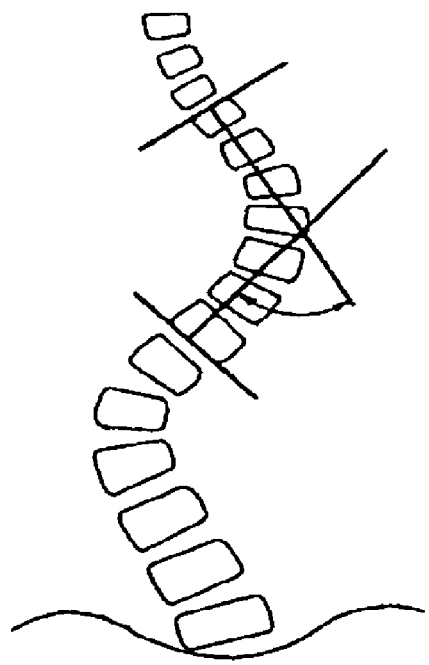
FIG. 5 shows the method of Cobb for measurement of the angle of scoliosis in the frontal full-spine radiograph.
Figure 7:
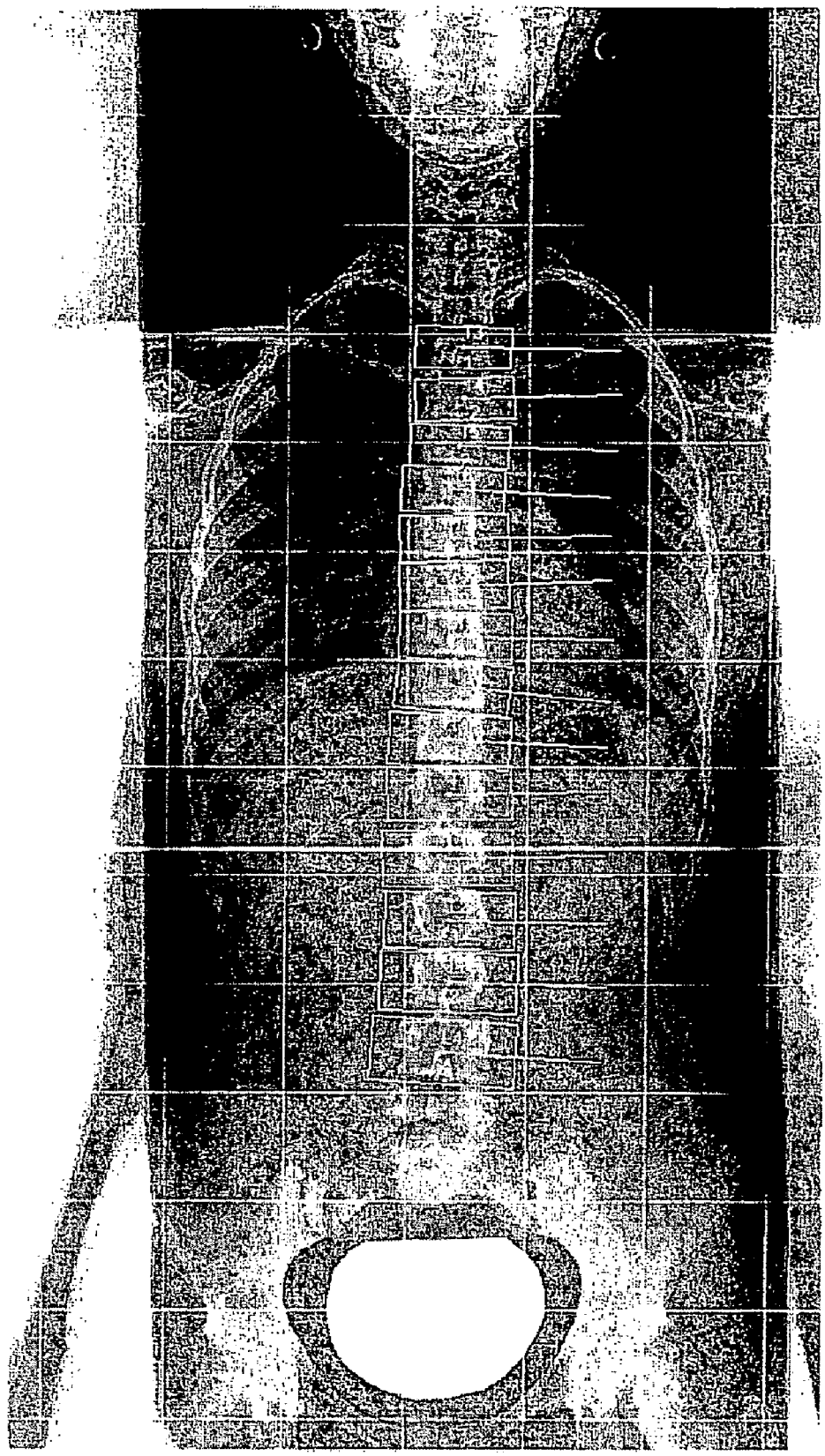
FIG. 7 shows a labeling of the vertebrae of a spinal column of a subject without scoliosis according to the registration method of the present invention. The angles of each of the vertebrae are calculated as the rotational component of the geometric transform, in contrast to the conventional manner of drawing tangent lines to the endplates of individual vertebrae.
Figure 8:
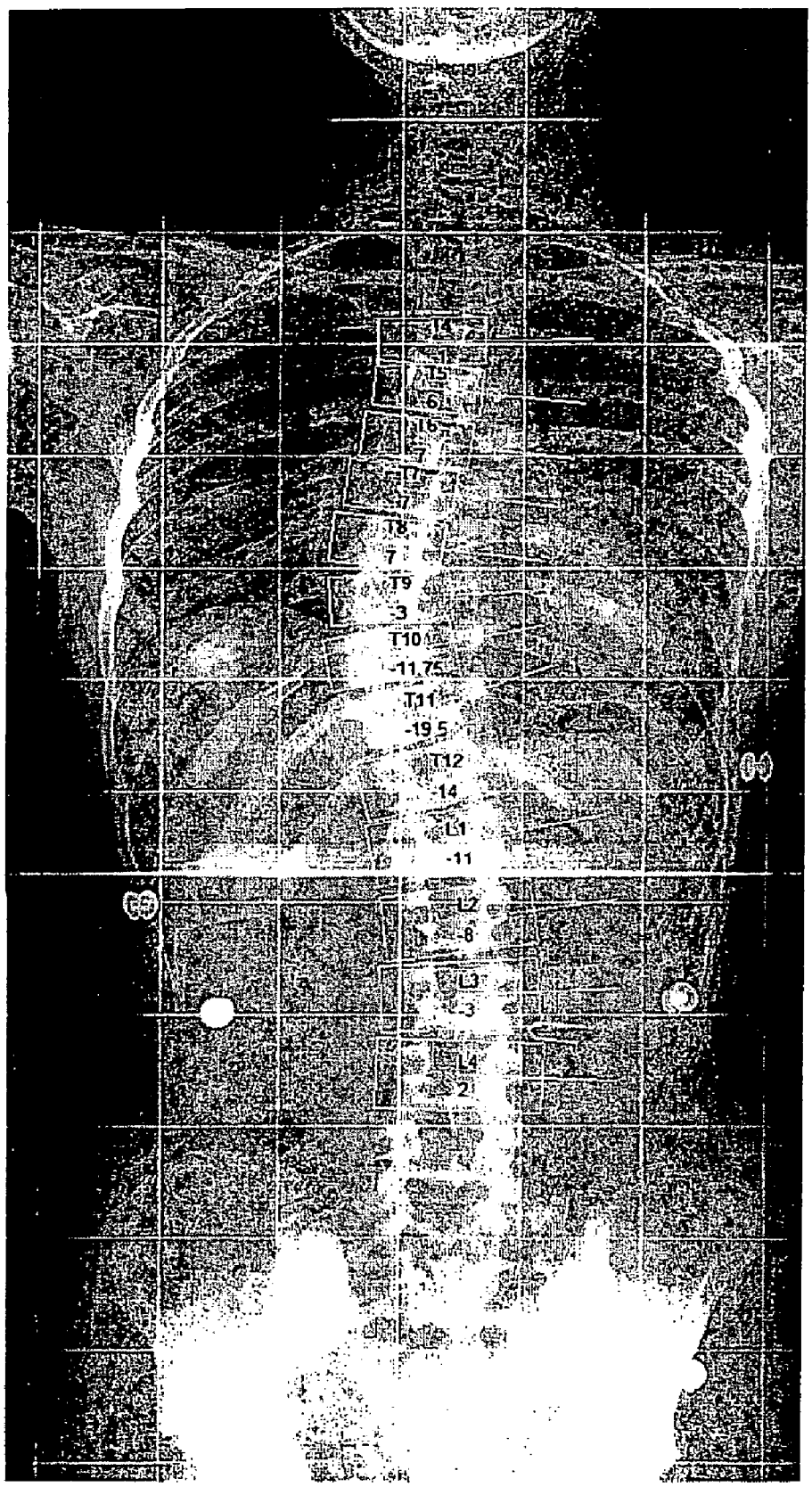
FIG. 8 shows a computation of the angle of Cobb according to the present invention. The angle of Cobb between the most inclined vertebrae of the curved segment is 26.5 degrees. The angle of Ferguson may be computed using the positions of the displayed midpoints of the vertebral body. These auto-placed midpoints are computed as a mapping result of the geometric transform applied to the model vertebra at optimal superimposition.

Image superimposition (also referred to as registration or alignment) of two images involves (1) obtaining a digital representation of the images that will be superimposed, (2) applying a geometric transform to one of the images (3) computing a similarity measure and (4) adjusting the parameters of the geometric transform according to a search strategy in order to optimize the similarity measure and re-iterate from step 2.

Each of these four key components of registration is discussed in the context of the present invention of superimposing (aligning) two radiographs. This step may precede a step of blending (also called fusing) the images.
Selection of the Type of Image Information The methods of registration that will be outlined in the sequel can be divided into two main categories based on the type of image information that is used in the registration: intensity-based methods and feature-based methods. The result of registration is that the images look similar to one another at all positions of interest.

Intensity-based methods use the pixel gray values in the matching process. The pixel gray value of one of the images to be registered may be modified to have similar intensity statistics as the other image. A typical modification is a bias and gain correction. The bias accounts for any global intensity or level difference between both images, the gain will correct a dissimilar range or window of the intensity values by applying a scaling factor. The scaling may be a nonlinear function, and may be applied to different levels of a multiscale decomposition of the image such as disclosed in EP 527 525. Intensity modification is typically implemented in the form of a look-up table.

Still belonging to the class of intensity-based methods are methods that start from derivatives of the gray value function. Because bony structures in radiographs are characterized by high gradients, and alignment of two radiographs is basically achieved by bringing the bony structures into register, it is plausible to apply differentiation to the original pixel intensities, i.e. to compute the partial derivates $\partial A/\partial x$, $\partial A/\partial y$ and $\partial B/\partial x$, $\partial B/\partial y$ and combinations of them such as gradient magnitude $$A' = \sqrt{\left(\frac{\partial A}{\partial x}\right)^2 + \left(\frac{\partial A}{\partial y}\right)^2}, \; B' = \sqrt{\left(\frac{\partial B}{\partial x}\right)^2 + \left(\frac{\partial B}{\partial y}\right)^2}$$

Gradients due to smoothly varying (low-frequency) structures such as soft tissue will have small gradient magnitude and will contribute less to the matching measure.

Feature-based methods use salient landmark features in the images that have been obtained by applying feature detectors and segmentation procedures. Typical features include edges obtained by first derivative maxima selection or second derivative zero crossings. The amount of data to process by the registration method is substantially reduced, at the expense however that the registration method has to be made robust to errors in the segmentation process.

In the sequel the intensity similarity measures that are used in the context of the present invention are detailed. It is assumed that an image B (the floating image) is spatially mapped into image A (the reference image), and the similarity measure is computed inside an overlap region R. When the image B is confined to an extracted region of interest, its spatial mapping into image A will generally fully lie within image A, and the area of the overlap region is constant and equal to the area of the region of interest (ROI). The ROI represents for example a specific vertebra in a spinal radiograph, in this example referred to as image B, that has to be registered onto its corresponding vertebra in a reference image A.

Selection of Corresponding Structures

To initialize the parameters of the geometric transformations, corresponding anatomical structures must be selected.

For example, to register two corresponding vertebrae of a flexion and an extension image, suitable corresponding landmark points may be selected to derive the initial spatial transformation. Because the exact spatial translation that will completely align both vertebrae will be sought by a search strategy in the space of admissible geometric transformation parameters, the correspondence need not be exact. Therefore, the selection of corresponding structures may be effectuated by a number of mouse clicks pairs in the vicinity of the corresponding landmarks on both images, for example a pair of points inside the vertebral body. Because not all detail may be equally visible on the radiographs, the user may opt selecting the most contrasting features, for example points on the bony cortex of the vertebrae. In the described example, the selection process is repeated for all vertebrae that must be matched.

In one embodiment, after selection of the landmarks, a region of interest (ROI) may be extracted in one of the images. This image is referred to as the floating image, because the geometric transform is applied to it, to map it into the reference image. The ROI is initially positioned over the reference image in accordance with the initial parameters of the geometric transformation, to determine the corresponding ROI. Intensities in the overlapping ROI's are subsequently used in the alignment similarity measure.

The shape of the ROI needs not necessarily take the outline of a diagnostic structure to be matched, for this would require explicit segmentation. It may be a rectangular or circular object that sufficiently encompasses the structure so as to enable accurate registration. The ROI area may furthermore be sparsely sampled to speed up the registration.

The selection process may be a manual process but can alternatively also be an automated process.

The initial parameters may for example be parameters defining a translation that maps corresponding landmarks onto each other and zero rotation.

Geometric Transformations

Aligning the two images requires that the floating image B be geometrically transformed and re-sampled prior to superimposing it onto the reference image A.

There are many different types of geometric transforms that are applicable, such as the ones described in copending European patent is application EP 04/076454.

An example of a very suitable transformation is the Euclidean similarity transformation, consisting of translations and in-plane rotations. This transform establishes a congruency relationship that preserves angles and lengths.

The imaging process of planar projection radiography can be modeled as a central (perspective) projection from X-ray source onto a plane detector. In the film-based art, the images cannot undergo a perspective projection to alter the viewpoint or patient pose, but the geometric transformation process is constrained to be a rigid body motion.

However, the image superimposition method according to the present invention may include all parameters of perspective imaging model, governed by a linear 3×3 transformation in homogeneous coordinates (termed homography). The following elements of imaging geometry may therefore additionally be taken into account:

Scaling one image with respect to the other: When the radiographs are projection images acquired from a same patient but at different times, the image may have undergone slight scaling differences because of patient movement in the source-detector direction (perpendicular to the projection plane). This fourth parameter offers one additional degree of freedom in the Euclidean similarity transformation.

Perspective distortion due to viewpoint differences: The 3D angle of incidence of the X-ray beam relative to the 3D patient pose may also have changed due to patient motion. Eight parameters determine the projective transform that describes the geometry of this imaging model, that is, two for translation, one for rotation, one global scale parameter, two parameters corresponding to a shearing (skew) and two parameters corresponding to a perspective distortion, For large X-ray source-detector distance the perspective imaging model may be approximated by an orthographic model, which comprises the skew parameters of an affine transformation but not the perspective parameters of a fully projective transformation. Although physically grounded in the imaging process of planar projection radiography, it is obvious that it is impossible with the film-based superimposition to apply such general linear transform to one of the images to align it with the other.

Non-rigid deformations between both images can be modeled also to account for geometric differences when landmarks are embedded in soft-tissue that alters its position in a geometrically non-linear way, or to describe global image deformations from a composition of a multitude of local deformations.

The computation of linear (Euclidean, affine, projective) and non-linear mappings (describing non-rigid body transformations) from point correspondences is described in the above mentioned European patent application the contents relating to these transformations being incorporated into the present application by reference.

In order to reduce variability which might originate from the selection of the initial parameters of the geometric transformation, multi-resolution search strategies can be used to cope with local extremes in the search space as will be explained below.

Interpolation and Re-Sampling:

Applying the geometric transform requires interpolation between existing sample points. For the similarity measure must be evaluated during the search strategy for many sets of parameters of the geometric transform, a fast and reasonably accurate algorithm is used, such as bilinear interpolation. When the optimal parameter set of the geometric transform is reached, a more accurate interpolation based on sinc approximation is switched to, so that final image quality is retained to the maximum.

Computation of the Initial Parameters of the Geometric Transform

The computation of the initial geometric transformation is effectuated using the correspondences between the objects representing similar anatomic entities. These objects will typically be easy to locate and be few in number.

Easily locatable structures are anatomic point landmarks, such as corners, midpoints of regions, bony edge junctions.

Correspondence of one anatomic landmark will allow computing the initial translation component of a rigid body transformation. The rotational component is not determined in that case, and will typically be set as the angle associated with aligned coordinate axes of image A and B.

For the user is not able to exactly point to identical landmarks, these points will only serve as a means to establish the initial transformation. During the automatic alignment, these points will in generally diverge slightly from each other and will not coincide exactly in the aligned images.

Intensity-Based Similarity Measures

In the floating image B, a ROI may be selected around the user defined anatomical landmark. This ROI may be rectangular or circular in shape. The latter shape has the advantage that it selects all points within a given distance from the user-defined point. This ROI is mapped into the reference image A using the initial parameters of the geometric transform, and its pixel-wise similarity with the pixels of image A are computed according to similarity measures outlined in the sequel. According to a search strategy, the geometric parameters are updated, and the accordingly transformed ROI of image B is again compared with image A until the best match is found. In the sequel different similarity measures that are applicable to compare the photometric content of two images are outlined and ordered with respect to their capability to cope with inter-image differences, such as bias and gain, but that are not attributable to spatial misalignment.

Mean Squared Difference:

A basic registration formula that reflects the notion of similarity is the sum of squared differences between image A and image B in the overlap region $(x,y) \in R$, which measure must be minimized, $$D = \frac{1}{N} \sum_{(x,y) \in R} (A(x, y) - B(x, y))^2$$

The sum of squares of differences may be replaced by the sum of absolute differences, i.e.

$$A = \frac{1}{N} \sum_{(x,y) \in R} |A(x, y) - B(x, y)|$$

N represents the number of pixels in the overlap area, which quantity may vary in general during the alignment procedure.

When the image B is geometrically transformed so that it is everywhere aligned with image A, the differences between the corresponding intensities will be smallest, and the least squares measure D will tend to zero. The difference is largest when all values of A are maximal and all corresponding values of B are minimal (which may be assumed to be 0 without loss of generality). The measure D can thus be normalized as follows $$D' = \frac{\sum_{(x,y) \in R} (A(x, y) - B(x, y))^2}{\sqrt{\sum_{(x,y) \in R} A^2(x, y)} \sqrt{\sum_{(x,y) \in R} B^2(x, y)}}$$

When the image B is a region of interest (ROI) that has much smaller size than the extent of image A, such that it is comprised everywhere in the spatial domain of image A, the energy $$\sum_{(x,y) \in R} B^2(x, y)$$

can further be regarded as a constant. The measure D can therefore be normalized to have a value 0<D<1 when it is divided by the local energy of image A.

$$D'' = \frac{\sum_{(x,y) \in R} (A(x, y) - B(x, y))^2}{\sum_{(x,y) \in R} A^2(x, y)}$$

However, as stated before, to account for global intensity shifts, the images should preferably be radiometrically corrected to have equal offset and gain (corresponding to equal level and window). In particular the least squares measures do no cope with inter-image bias and scaling. Different ways to achieve additive and multiplicative invariance are outlined hereafter. One method is to modify the window and level of the images prior to registration. A two-point correction scheme can be used based on the histogram of the images, one to fix the zero point (the offset) and the other typically at 50% of saturation (to calculate the gain). Another approach is to explicitly take the offset and scale parameters into account in the optimization strategy. The scaled least squares measure reads as $$D'(s) = \frac{\sum_{(x,y) \in R} (A(x, y) - sB(x, y))^2}{\sqrt{\sum_{(x,y) \in R} A^2(x, y)} \sqrt{\sum_{(x,y) \in R} s^2 B^2(x, y)}}$$

Finally, similarity measures may be used that achieve additive and multiplicative invariance directly. These measures are described in the sequel.

Normalized Cross-Correlation:

The measure D, D' and D" can be expanded into their quadratic terms. The energy of the floating image (corresponding to a constant ROI) is constant, the energy of the reference image in the varying region of overlap may be regarded as approximately constant. Hence, the quadratic terms corresponding to the image A and image B do not affect the minimization of the measure D or D', so that a similarity measure is obtained which depends on the product or cross-correlation of images A and B, which measure must be maximized $$C = \frac{1}{N} \sum_{(x,y) \in R} (A(x, y)B(x, y))$$

$$C' = \frac{\sum_{(x,y) \in R} (A(x, y)B(x, y))}{\sqrt{\sum_{(x,y) \in R} A^2(x, y)} \sqrt{\sum_{(x,y) \in R} B^2(x, y)}}$$

$$C'' = \frac{\sum_{(x,y) \in R} (A(x, y)B(x, y))}{\sum_{(x,y) \in R} A^2(x, y)}$$

If the images are identical, the normalized cross-correlation will be equal to 1. As with the sum of squared differences measure, this measure does not explicitly compensate for differences in image intensity, and it is possible that images identical except for global scaling do not reach an optimum in the cost function unless a variable scaling parameter is formally included in the model. Furthermore, if the image energy associated with varying overlap region associated with the reference image varies with position, the matching based on the cross-correlation can fail. For example, the correlation between a feature and an exactly matching region in the image may be less than the correlation between the feature and a bright spot.

The computation of the correlation measure C can be speeded up significantly by the use of the Fourier transform of the images. The Fourier transform of the un-normalized correlation of two images is the product of the Fourier transform of one image and the complex conjugate of the Fourier transform of the other. The rigid body motion associated with film-based superimposition has an equivalent in the Fourier domain. The translation introduces a phase shift in the Fourier components but does not alter the amplitudes. The rotation rotates the Fourier plane over an equal amount, and the offset shift affects only the DC component. Minor slowly varying scale changes can also be accommodated for they introduce noise concentrated at low spatial frequencies. The translation property may be used in a method referred to as phase correlation, to align images that are only shifted relative to one another. Such images have similar Fourier magnitudes, but show a phase difference that is related to the amount of displacement $(d_x, d_y)$. The transform coefficients are normalized to unity prior to computing the correlation in the frequency domain $(u,v)$, given by the expression $$\frac{F_A(u, v)F_B^*(u, v)}{|F_A(u, v)||F_B^*(u, v)|} = e^{(u d_x + v d_y)}.$$

The inverse Fourier transform of this expression, also called the cross-power spectrum phase, will show a peak at the requested displacement. Since each component has unit magnitude, and thus the phase difference of each frequency component contributes equally, the location of the peak will not change substantially if there is noise limited to a narrow frequency interval. Hence, this Fourier method achieves excellent robustness against correlated and frequency-dependent noise. In the presence of white noise, which corrupts all frequencies and distorts the peak, maximizing the spatial correlation measure C is optimal. When the misalignment also includes a rotational component, the rotation angle may be computed as the angle, which makes the inverse Fourier transform of the cross-power spectrum phase close to an impulse, and the translation is subsequently taken as the spatial displacement of the impulse.

Normalized Covariance:

A measure which is related to cross-correlation, that does account for offset differences (inter-image bias), and that measures correlation on an absolute scale ranging from −1 . . . 1 is the normalized covariance measure $$E = \frac{1}{N} \sum_{(x,y) \in R} (A(x, y) - \overline{A})(B(x, y) - \overline{B}) = \mathrm{VAR}(A(x, y) \cdot B(x, y))$$

$$E' = \frac{\sum_{(x,y) \in R} (A(x, y) - \overline{A})(B(x, y) - \overline{B})}{\sqrt{\sum_{(x,y) \in R} (A(x, y) - \overline{A})^2} \sqrt{\sum_{(x,y) \in R} (B(x, y) - \overline{B})^2}}$$

$$= \frac{E}{\sigma_A \sigma_B} = \frac{\mathrm{VAR}(A, B)}{\sqrt{\mathrm{VAR}(A) \cdot \mathrm{VAR}(B)}}$$

When the observed covariance of paired gray values is as high as the possible covariance, the correlation will have a value of 1, indicating perfectly matched order of the two variables (gray values). A value of −1 is perfect negative co-variation, matching the highest positive values of one variable with the highest negative values of the other. The normalized covariance measure thus is a symmetrical measure of linear dependence between the gray values in the overlap region of image A and image B, i.e. the entries in the co-occurrence matrix of joint gray values i in image A and j in image B lie on a straight line.

Instead of computing cross-correlation of the raw intensity pixel values, it may be applied on the gradients of intensity A' and B'. The edges of bony structures are characterized by high gradients and associated high spatial position information. Therefore, they will contribute significantly to the correlation similarity measure when both images are aligned. The low spatial frequencies caused by soft tissue, which image appearance may vary between two image acquisitions, will be filtered out by the gradient computation, and hence will not contribute to the correlation measure.

Ratio Image Uniformity:

A measure, which is related to cross correlation, that does account for scaling differences, is calculated by the ratio uniformity measure, which is based on the image of divisions of corresponding pixel values of image A and B. When the images A and B are in perfect alignment, the resulting ratio image will be a constant image. It means that each gray level maps to exactly the same gray level in the other image. The ratio similarity measure hence measures the standard deviation of the ratio image, and divides it by the mean ratio to achieve multiplicative invariance.

$$Q(x, y) = \left.\frac{A(x, y)}{B(x, y)}\right|_{(x,y) \in R}, \overline{Q} = \frac{1}{N} \sum_{(x,y) \in R} Q(x, y)$$

$$R = \frac{\sqrt{\frac{1}{N} \sum_{(x,y) \in R} (Q(x, y) - \overline{Q})^2}}{\overline{Q}}$$

Partitioned Intensity Uniformity:

The measure is related to the ratio image uniformity and is based on the following grounds. Due to noise and soft tissue structures, all pixels having a certain intensity i in image A will map to a set of clustered intensities in the registered image B. When there is a functional dependence between the intensities of A and B, there will only be one cluster per iso-set i of image A. Obviously, when the images are perfectly aligned, the dispersion or standard deviation of each cluster is minimal. Multiplicative invariance is achieved by dividing each term in the sum by the mean of the cluster. This measure is more general than cross correlation because it only assumes that intensity dependence can be represented by some function. The spatial coherence may be retained in the measure by partitioning the ROI image B into a number of intensity iso-sets, i.e. areas of similar intensity. The boundaries of these areas are placed over the image A, and the variance and mean of each area in image A is computed. The expression for this similarity measure, which must be minimized, is $$W = \frac{1}{N}\sum_i N_i \frac{\sigma_i}{m_i}$$

with N the number of pixels in the overlap area R, $N_i$ the number of pixels in the iso-intensity set i, and $\sigma_i$ and $m_i$ the standard deviation and mean of the intensities in the corresponding set in image A (the image into which the position of the ROI image B has to be searched). The relative areas $N_i/N$ constitute the weights in this measure.

The measure W will generally give different results when computed on image B. For B represents a ROI in the second image, the ensemble of pixels of image B will normally completely overlap with image A as it is continually moved over it, hence the statistics of image B will not alter. Therefore, the measure must be computed on the basis of the changing overlap region in reference image A, when the floating image B only contains a ROI.

For digital radiographs are typically quantized to the 12-bit range, the iso-intensity sets may be too sparsely populated to compute reliable statistics. Grouping the intensities into more coarsely quantized bins can alleviate this effect.

Correlation Ratio:

A correlation ratio measure related to the measure W is obtained by normalizing with the global variance of the overlap region. This global normalization makes the measure more stable with respect to the spatial transformations, hence the correlation ratio is smoother and easier to optimize, and also sub-samples more smoothly. The expression for this similarity measure, which must be minimized, is $$CR = \frac{1}{N\sigma^2}\sum_i N_i \sigma_i^2$$

Minimizing only $$\frac{1}{N}\sum_i N_i \sigma_i^2$$

is not sufficient, because this term can be low for two reasons: first the reference image A is well explained by the spatially transformed image B, i.e. the cluster corresponding to the iso-intensity set i has low variance $\sigma_i$, or image A contains little information in the overlap region, i.e. the variance $\sigma^2$ of image A in the overlap region is low. Thus only minimizing $$\frac{1}{N}\sum_i N_i \sigma_i^2$$

would tend to disconnect the images, i.e. the variance of the overlap region in image A, determined by the spatially transforming image B, is not taken into account. Thus when the ROI image B is overlapping with a flat region in image A, its similarity with image A will be penalized by the correlation ratio because the overlap region in A has low variance.

Similar to the ratio uniformity measure, the direction of the mapping is important, i.e. choosing to minimize variance in either image A or image B may lead to a different result. Indeed, one image may delineate significantly more regions than the other, and so every iso-intensity set would map to only one intensity value in the other, having a zero associated variance. For the task of aligning radiographs, this will normally be uncommon, since both images normally come from the same modality with high dynamic range (typically 12 bit).

Mutual Information:

A similarity criterion, that is still more general than the ratio criterion, for it assumes no functional dependence between the image intensities is implemented by the mutual information criterion. Mutual information is independent of offset and gain shifts for a mapping is established between (sets of) gray levels of the images A and B. Hence, in contrast to correlation which assumes a linear relationship between the pixel intensity values of the two images, mutual information instead searches for the most probable co-occurrence of intensity values between both images. This measure makes no assumption regarding the nature of the relationship that exists between the image intensities, i.e. it does not assume a linear, nor functional correlation, but only a predictable or statistical relationship. Hence, high valued intensities may for example be paired with low-intensity values at final registration. This feature is useful for X-ray matching as the images are formed by projection, and hence, when the viewing direction of X-ray source to detector, or the patient pose was different between acquisition of image A and image B, non-linear intensity relationships may result at geometrically equivalent positions in both images. As no re-projection can be performed to restore identical imaging conditions and the linear relationship between image A and B, mutual information is a suitable similarity model to cope with projection artifacts.

The mutual information or relative entropy, to be maximized, is defined as $$I(A, B) = H(A) + H(B) - H(A, B)$$

$$= \sum_{i \in A}\sum_{j \in B} p_{AB}(i, j)\log\frac{p_{AB}(i, j)}{p_A(i)p_B(j)}$$

where p(i) and p(j) are the marginal probability distributions in the individual images A and B, computed from the intensity histograms in the overlap region, and p(A,B) is the joint probability distribution, computed from the co-occurrence matrix between spatially corresponding gray values i and j in the overlap region of image A respectively B. The marginal probability distributions are the projections of the joint probability distribution on the axis corresponding to the intensities in A and B. Joint and marginal distributions vary during registration because the overlap region continually changes as the geometric transformation parameters change. The entropies H(A) and H(B) defined as $$H(A) = -\sum_{i \in A} p_A(i)\log p_A(i)$$

$$H(B) = -\sum_{i \in B} p_B(i)\log p_B(i)$$

consider the information that is contained in and contributed by the overlapping region of each image. The third term in the mutual information measure is the joint entropy H(A,B)

$$H(A, B) = -\sum_{(i,j) \in R} p_{AB}(i, j) \log p_{AB}(i, j)$$

This measure, which must be minimized, is an unreliable measure when it is used without the image entropy terms, for it involves the implicit assumption that large regions in the two images should increase their overlap as the images approach registration. Large regions of constant intensity occur easily in radiographs, such as is direct exposure and collimation regions, and the joint entropy would seek to maximize the overlap of such constant intensity regions for it reduces the joint entropy of the joint histogram. Excluding direct exposure and collimation regions from the joint histogram using a segmentation algorithm such as e.g. disclosed in EP 610 605 and EP 887 769 may be used to lessen the influence of them.

Although better than joint entropy, mutual information reduces this heavily dependence on large regions, but cannot completely rule it out. Normalizations that are more overlap independent are $$\tilde{I}(A, B) = \frac{2I(A, B)}{H(A) + H(B)}$$

$$\tilde{I}(A, B) = H(A, B) - I(A, B)$$

$$\tilde{I}(A, B) = \frac{H(A) + H(B)}{H(A, B)}$$

As with the ratio measures, the computation of the joint histogram (co-occurrence matrix) may require re-binning of the original intensities into fewer levels in order to yield reliable joint statistics. The variables i and j may thus either represent the original image intensities or the re-quantized intensity bins.

Search Strategy

The correspondence problem can be stated as finding the set of parameters p of the geometric transform (rotation, translation and spatial scale) and intensity transform (alfa, beta) that maximize a similarity cost function (or minimize it, depending on the measure)

$$p^* = \underset{p}{\operatorname{argmax}} C(p)$$

A search strategy chooses the next geometric transformation from the class of admitted transformations. The image B is then subjected to the geometric transformation and re-sampled by interpolation to yield a transformed image B'. Finally the new similarity measure between image A and B' is computed, which will be better in the case the direction in search space effectively, was towards the optimal set of parameters. Special attention has been paid to problems inherent to optimization in the context of the present invention, such as the occurrence of the following items.

Unwanted Local Minima in Search Space:

Special provision may be made to avoid traps in local minima (or maxima, depending on the sense of the similarity measure). Standard mathematical optimization such as gradient descent or Powell's direction set method may get stuck in local minima. The global minima will normally correspond to a mapped ROI that still lies in the vicinity of the ROI mapped according to the initial parameters of the geometric transformation. This initial mapping is centered on the floating ROI's corresponding point in the reference image A. Therefore, an exhaustive search, trying all possible combinations of geometric parameters, may be performed, and the combination associated with the global minimum determines the solution. An alternative that also finds the global minimum at a much lesser computational cost is simulated annealing.

Unwanted Asymptotic Behavior in Search Space:

The search space spanned by the parameters of the geometric transformation may be limited in order to prevent unwanted asymptotic behavior of the cost function. For example, when using large translations, the overlap between the images becomes very small, which in the case of registering a ROI of radiograph B within radiograph A is very unlikely. Very large rotation angles, large scale factors, or large skew and perspective distortion factors will also be unlikely. The correct behavior is obtained in these cases by associating large costs to these conditions.

Multi-Resolution Optimization:

The optimization scheme can be speeded up significantly by a hierarchical or multi-resolution scheme. A coarse resolution version of each of the images A and B are computed, e.g. by calculating the Gaussian pyramidal decomposition of the image (as has been described in EP 527 525), and selecting a coarse level, which has a reduced number of pixels due to sub-sampling. The starting estimate of the parameters is fixed by establishing an initial positional correspondence between both images e.g. by letting the user select two corresponding structures. Clicking at least one pair of corresponding points in image A and image B can do the selection. The initial transformation is then computed as outlined incopending European patent application 04/076454. The similarity measure is evaluated on the coarse resolution versions at that starting estimate of the parameters, and with a single increment in each parameter of the spatial or radiometric transformation model. All combinations of single increment parameter modifications are tried. The best combination is chosen and the algorithm iterates until no step can be found that improves the similarity measure. When the algorithm is finished at a given resolution, the next higher resolution levels of the image pyramids are selected, and the search process is initiated again, starting from the transformation parameters set computed on the previous level. As the resolution is increased, the step size may be reduced to provide a sub-pixel registration solution.

Multi-resolution techniques require that the images contain sufficient low frequency information to guide the initial stages of the search towards the basin of algorithm convergence around the global optimum. This condition is met by the medical images considered in the context of the present invention for the image content may be characterized by spatially varying background signal with superimposed diagnostic detail.

The multi-resolution or hierarchical strategy is useful to cope with image noise and clutter and irrelevant image detail that may possibly create local optima in the search space. Furthermore, the result of gradient descent on a coarse scale is not necessarily the final solution, for it is known that first, second and higher derivatives measures on a coarser scale delocalize feature points, such that optimal positions in the coarser levels must be tracked towards their final position in the finer scale levels.

An alternative way to speed up the intensity-based registration algorithm is to only compute the cost function for some sub-set of the pixels in the overlap region between both images.

Extraction of the Rotational Component(s) of the Geometric Transform

The search strategy aims at adapting the parameters of the geometric transform until the optimal set is found. Two tracks may be considered for obtaining the rotational component(s) θ of the transform: (a) adapting the parameters S, $\theta_i$, $T_i$ of the elementary geometric operations individually, requiring one has immediate control over the value of the applied rotation (and the other parameters), or (b) adapting directly the parameters a ... f of the overall transform, requiring a decomposition to extract the rotational component (and other components).

The decomposition is derived hereafter for the Euclidean case, for it physically represents a rigid body transformation.

Euclidean Case

Euclidean mappings offer four degrees of freedom, in the case of isotropic scaling, and are able to map a bounded line segment into a bounded line segment (with different lengths and orientations). These mappings are also termed rigid body transformations. A rigid to body transformation consists of a composition of a rotation about the origin over an angle θ w.r.t. the x-axis in the counterclockwise direction, followed by a translation $(T_x, T_y)$ w.r.t. the origin and scale factors $S_x, S_y$ ... applied to the coordinates x and y:

$$T_E = \begin{pmatrix} S_x & 0 & 0 \\ 0 & S_y & 0 \\ 0 & 0 & 1 \end{pmatrix} \begin{pmatrix} 1 & 0 & T_x \\ 0 & 1 & T_y \\ 0 & 0 & 1 \end{pmatrix} \begin{pmatrix} \cos\theta & -\sin\theta & 0 \\ \sin\theta & \cos\theta & 0 \\ 0 & 0 & 1 \end{pmatrix}$$

Scaling T to have a non-unity term $a_{33}$ can reduce the 5 variables in this mapping to 4.

Considering isotropic scaling by a factor S, the combined Euclidean mapping can be written as $$T_E = \begin{pmatrix} S\cos\theta & \sin\theta & T_x \\ -\sin\theta & S\cos\theta & T_y \\ 0 & 0 & 1 \end{pmatrix}$$

In three dimensions, a rigid body transformation is characterized by six degrees of freedom (three translation components preceded by three rotations around each of the image axes in the counterclockwise direction)

$$T_E = T \cdot R$$
$$= T \cdot R_x \cdot R_y \cdot R_z$$
$$= \begin{pmatrix} 1 & 0 & 0 & T_x \\ 0 & 1 & 0 & T_y \\ 0 & 0 & 1 & T_z \\ 0 & 0 & 0 & 1 \end{pmatrix} \begin{pmatrix} 1 & 0 & 0 & 0 \\ 0 & \cos\theta_x & -\sin\theta_x & 0 \\ 0 & \sin\theta_x & \cos\theta_x & 0 \\ 0 & 0 & 0 & 1 \end{pmatrix} \begin{pmatrix} \cos\theta_y & 0 & \sin\theta_y & 0 \\ 0 & 1 & 0 & 0 \\ -\sin\theta_y & 0 & \cos\theta_y & 0 \\ 0 & 0 & 0 & 1 \end{pmatrix} \begin{pmatrix} \cos\theta_z & -\sin\theta_z & 0 & 0 \\ \sin\theta_z & \cos\theta_z & 0 & 0 \\ 0 & 0 & 1 & 0 \\ 0 & 0 & 0 & 1 \end{pmatrix}$$

$$= \begin{pmatrix} \cos\theta_y\cos\theta_z & -\cos\theta_y\sin\theta_z & \sin\theta_y & T_x \\ \sin\theta_x\sin\theta_y\cos\theta_z + \cos\theta_x\sin\theta_z & -\sin\theta_x\sin\theta_y\sin\theta_z + \cos\theta_x\cos\theta_z & -\sin\theta_x\cos\theta_y & T_y \\ -\cos\theta_x\sin\theta_y\cos\theta_z + \sin\theta_x\sin\theta_z & \cos\theta_x\sin\theta_y\sin\theta_z + \sin\theta_x\cos\theta_z & \cos\theta_x\cos\theta_y & T_z \\ 0 & 0 & 0 & 1 \end{pmatrix} T$$

The matrix $R_z$ represents a rotation in the counterclockwise direction around the z-axis, $R_y$ and $R_x$ represent rotation around the y- and x-axis respectively. The angles of rotation are the so-called Euler angles. The matrix T represents three-dimensional translation.

Referring to the two-dimensional case, the matrix $T_E$ holds only 4 unknowns and can be re-written as $$T_E = \begin{pmatrix} a & b & c \\ -b & a & f \\ 0 & 0 & 1 \end{pmatrix}$$

The coefficients may now be equated to the coefficients of $T_E$ written in terms of the concatenated elementary geometric operations to determine constituent components of translation, scaling and rotation.

Following the principles of algebra, these components are determined as:

$$T_x = c$$

$$T_y = f$$

$$S = \sqrt{a^2 + b^2}$$

$$\theta = \arccos(a/S)$$

The last equation represents the rotational component searched for.

Similarly, in three dimensions, a rigid body transformation has 6 degrees of freedom, and may be decomposed to retrieve the rotational components $\theta_x$, $\theta_y$, $\theta_z$.

The translations are trivially extracted as $T_x = T_{E_{1,4}}$, $T_y = T_{E_{2,4}}$, $T_z = T_{E_{3,4}}$. Inspecting the rotation matrix R, the rotation $\theta_y$ can be extracted to as $\theta_y = \arcsin(R_{1,3})$. If $\cos(\theta_y) \neq 0$, $\theta_x$ is derived from $R_{2,3}$ and $R_{3,3}$, and $\theta_z$ is derived from $R_{1,1}$ and $R_{1,2}$. If $\cos(\theta_y) = 0$ (meaning a rotation around the y axis with angle $$\theta_y = \pm \frac{\pi}{2}),$$

R reduces to $$R = \begin{pmatrix} 0 & 0 & \pm 1 & 0 \\ \pm\sin\theta_x\cos\theta_z + \cos\theta_x\sin\theta_z & \pm\sin\theta_x\sin\theta_z + \cos\theta_x\cos\theta_z & 0 & 0 \\ \pm\cos\theta_x\cos\theta_z + \sin\theta_x\sin\theta_z & \pm\cos\theta_x\sin\theta_z + \sin\theta_x\cos\theta_z & 0 & 0 \\ 0 & 0 & 0 & 1 \end{pmatrix}$$

$$= \begin{pmatrix} 0 & 0 & \pm 1 & 0 \\ \sin(\theta_z \pm \theta_x) & \cos(\theta_z \pm \theta_x) & 0 & 0 \\ \cos(\theta_z \pm \theta_x) & -\sin(\theta_z \pm \theta_x) & 0 & 0 \\ 0 & 0 & 0 & 1 \end{pmatrix}.$$

This matrix determines the quantity $\theta_z \pm \theta_x$ from $R_{2,1}$ and $R_{2,2}$; this physically means $\theta_x$ cannot be distinguished from $\theta_z$ because the x-axis is aligned with the z axis after the rotation $$\theta_y = \pm\frac{\pi}{2}$$

around the y-axis. In this case $\theta_x$ can be set to zero, and $\theta_z$ derived.

Superimposition and Blending

When the final geometric transformation is determined, it is applied to the floating image B to calculate the samples on the new positions in the overlap region R with image A. The result is that at each pixel location two intensities are available (1) the unmodified intensity of reference image A, and (2) the spatially transformed intensity $B^T$ of image B. This data representation is called the digital superimposition of image B onto image A, because both image data sets are represented in a common coordinate system. Outside the overlap region R, either the original image samples of image A or the transformed image sample of image $B^T$ are available. When the original images A and B were of the same size, the superimposition data representation would normally need to allocate larger row and column dimensions to accommodate full storage of the transformed image $B^T$ in the coordinate system of image A. A high image quality interpolation and re-sampling algorithm such as a sinc interpolator can be used to calculate $B^T$ in order to retain image sharpness of the transformed image to the maximum.

To blend image A and $B^r$, at each pixel in the blended image a suitable combination of the corresponding pixel in image A and $B^T$ is taken. The proportions of each image are preferably such that the blended pixel value does not exceed the maximal intensity. In the described embodiment the blended image is calculated in the overlap region R as $$Z(x,y) = mA(x,y) + (1-m)B^T(x,y)$$

with m the blending or mixing factor ($0 \leq m \leq 1$). m controls the influence of each input image in the blended result. When m=1 only image A will be displayed, when m=0, only $B^T$ will be shown. When images A and B have equal range and level, m will preferably be chosen around 0.5. This choice is made because the intensities in the ROI, which have been used to align the image, will typically be identical when image A and image B have no additive (offset, level) and multiplicative (scale, window) differences. However, when there exist window/level differences (and these do not influence the registration measures as outlined above), the images may be rescaled between minimal and maximal intensity using the ranges ($A_{min}, A_{max}$) and ($B_{min}, B_{max}$) of their respective histograms prior to blending them.

User Interface

A user interface may be constructed to interact and display with the registration procedure outlined above. It may comprise the following elements.

Means for Selection of Corresponding Structures:

The selection of corresponding structures serves to initialize the geometric transformation parameters. The means for selection of corresponding structures is for example a mouse and associated mouse cursor, the selection can be performed by pointing with a mouse cursor for example to identical anatomically well-manifested landmarks.

These landmarks may comprise points such as the approximate center of the vertebral body, corner points of the vertebral body, pedicle centers or landmark points on the processi spinosi.

By selecting one point, the translation parameters may be initialized. By selecting more points, more parameters can be initialized.

For example, selection of two corresponding points (e.g. the centers of both pedicles on a vertebra) may fully define an initial Euclidean similarity transform. Selecting three corresponding points initializes an affine transform. Selecting four corresponding points (e.g. the corner points of the vertebral body) may initialize a projective transform.

When multiple structures must be registered, such as all cervical vertebrae in a flexion and extension cervical spine examination, the final geometric transformation parameters of the current vertebral registration may serve to determine an initial guess of the geometric transformation parameters for the registration of the next vertebral pair based on a model of normal values for inter-vertebra geometry (e.g. inter-vertebral distance and relative rotation).

Display of Blended Images

Blending Control Slider:

The degree of blending m that is applied in the overlap area between image A and $B^T$ may be controlled by a slider, that enables the user to continually adjust the amount of visible information of image A or $B^T$. This feature is advantageous to selectively focus fully on either image A or image $B^T$. It is clear that such gradual blending is impossible in the prior film-based art.

Means for Manual Adjustment of the Geometric Transform Parameters:

In the current event that the registration result does not fully fulfill the diagnostic requirements, the user may manually adjust the results of the geometric transformation by means of a user interface, starting from the automatically computed solution.

Translations in x and y direction may be effectuated in a translation mode using for example the arrow keys, or dragging the mouse cursor.

Rotation of the floating image with respect to the reference image may be effectuated in a rotation mode by first selecting a center of rotation, and secondly selecting a point in the floating image that serves as a handle to rotate the floating image with respect to the reference image that stays fixed. The rotation angle may be continually computed as the angle line between the handle point and the center of rotation and the image x-axis. The handle point may be constrained to lie on a circle irrespective of the in plane movements of the cursor.

Because the distance of the line segment spanned by the center of rotation and the handle point does not affect the value of the rotation angle, this radius may be used to emulate scaling also. Using the up and down arrow keys will increase resp. decrease the radius of circular path of the handle cursor, thereby enabling a fine tuning of the scale.

Anisotropic scaling can be emulated also e.g. by using a square, and modifying the aspect ratio of it by dragging the vertical or horizontal borders. For zero rotation, the borders stay aligned with the image coordinate axes. To apply rotation, one of the corner points can be used as a handle to rotate the rectangle and the floating image will be rotated in a proportional amount.

Skewing along x and y direction and perspective distortions can be emulated also in a skew mode and perspective mode respectively. These modes depart from a displayed model square, which, to achieve sufficient parameter resolution, may encompass a substantial part of the floating image. In the skew mode, the corner points of the model square may be moved parallel to either the x-axis, to emulate skew of the floating image along the x-axis in an amount proportional to the motion of the corner point, or parallel to the y-axis, to emulate skew of the floating image along the y-axis in an amount proportional to the motion of the corner point. When the upper-right point is dragged to the right, the upper-left point will follow in the same amount, hence, skew applied to the square will deform the square to a parallelogram (with pair-wise parallel juxtaposed edges).

In the perspective mode, each of the corner points can also be moved parallel with a coordinate axis, but in contrast to the skew mode, the juxtaposed point will not follow, hence the associated edge pair will become non-parallel. This operation will introduce non-zero terms for the perspective components of the geometric transformation of the image and will deform a square into a quadrangle.

For each of these geometric transformation parameters may typically require small modifications, a suitable conversion factor may be set that downsizes the manual motion (of translation, rotation, scale, skew or perspective correction) to the effectively applied parameter.

Verification of the Registration Result:

The user can check the registration of the corresponding vertebrae of flexion and extension image by subtracting the registered images, and checking the remaining detail in the difference image. When two vertebrae exactly match, the matching image area in the overlap region will vanish. The absence of detail can be qualified by the sum of squared differences, expressed by the measure D as given above. Alternatively, the variance in the overlap region may be computed. Both of these measures must be low when good registration is achieved.

Application to Cervical Spine Examinations

Radiographic exposures of the extension lateral cervical spine position are combined with the flexion lateral position to evaluate segmental motion of the cervical spine for hypermobility or instability. Patients with post-traumatic neck pain, arthritis, and spinal fusion are commonly examined with these functional views.

Maximal Flexion-Extension Angle:

The range of maximal flexion-extension in the cervical spine is determined on the fused images with vertebral bodies of C7 registered. The angle is measured between the line tangent to the posterior margins of the vertebral bodies C1 ... C3, and is compared with its normal range.

The use of the blending control slider described higher is particularly advantageous to effectuate this type of measurement on the blended image. To draw the first tangent line to the posterior margins of the vertebrae in the flexion image, the slider is moved in a state such as to display only the first (flexion) image. In this way, structures of the second (extension) image that otherwise may obscure the particular image features of the first (flexion) image, on which the line construction is based, are absent. The second tangent line to the posterior margins of the vertebrae in the extension image is similarly drawn on it with the slider now moved in a state such as to display only the second (extension) image. Because both flexion and extension images are registered, the second line is actually drawn directly in the reference coordinate system of the first image, and hence the angle between first and second image is computed without the need of manually aligning the coordinate systems. This feature is clearly impossible with the prior art of film superimposition.

Motion Diagram:

The ranges of flexion and extension of the cervical spine are determined as angles in the motion diagram. The motion diagram may be constructed in a number of ways.

In one embodiment first vertebral bodies C7 in the flexion (floating) and extension (reference) view are selected, and registered according to the procedure outlined above. The angle $\alpha_7$ applied to the flexion (floating) image to bring it in register with the extension view is recorded. This angle may equivalently be recorded by drawing a reference line of the floating image (e.g. its x-coordinate axis) into the coordinate system of the reference image.

Next, vertebral bodies C6 in the flexion and extension views are selected, and registered. The angle $\alpha_6$ applied to the floating image is recorded, or equivalently its reference axis is drawn in the reference image coordinate system.

The angle between these first two lines indicates the range of movement between vertebras C7 and C6 and is denoted as C6-C7.

This angle can equivalently be computed as the difference of angles $\alpha_6 - \alpha_7$. Hence, the required angle, representing the segmental mobility, automatically results by extracting the rotational component of the geometric transformation matrix that is obtained when the corresponding vertebras are registered. It will be clear that this automatic result cannot be achieved with the prior art of film superimposition.

Thirdly, the angle may also be computed as the angle between corresponding tangent lines to the vertebral body C6 in the superimposed and blended flexion and extension images, with the vertebra C7 registered. For example, the dorsal tangent lines may be used to this purpose. Other tangent lines may be used depending on their degree of visibility in the images. To avoid obscuring details due to the superimposition, the blending control slider is used to selectively display either the flexion image or the extension image during drawing the lines.

The process, outlined above, is repeated by registering successively vertebras C5, C4, C3, C2, to yield the angles C5-C6, C4-C5, C3-C4, C2-C3. Jointly, these angles constitute the motion diagram, and the drawn diagram shows a typical shape in the case of normal cervical mobility. The angles are compared with their normal values to assess the presence of disease or injury.

A dynamic view of the cervical motion can be obtained by a motion image sequence in which the successive vertebral registrations are displayed quickly one after another.

Application to Frontal and Lateral Full-Spine Examinations

Radiographic exposures of the full-spine in frontal and lateral view are frequently performed to quantify the angulation of the spinal column.

In the frontal full-spine examination, the projection of the spinal column normally is a straight line; however, in scoliosis patients the spinal column projects as a lateral curvature, taking the form of an "S" or "C". Scoliosis is generally described as to the location of the curve or curves, as shown in FIG. Xxx. Primary or structural curvature, to be discriminated from the compensatory or non-structural curvature, is the one which cannot be changed significantly by bending to one side or the other or tilting the pelvis, and is assessed from additional radiographs with the patient bending to the left and right, or tilting the pelvis. The angulation of the curve(s) is measured conventionally by the method of Cobb or Ferguson.

The Ferguson method consists of the following steps. The end vertebrae of a curved segment are searched for; these vertebrae are situated at the end of a curved segment that is the least rotated and lie between the two curve segments. Next the apex vertebra is located; this vertebra is the most rotated vertebra at the peak of the curve (rotation of the vertebra is commonly assessed by looking at the relation of the pedicles to the midline). In each of these three vertebrae, the centre of the outline of the vertebral body is marked with a dot. Finally, lines are drawn from the apex to each end vertebra, and the Ferguson angle of the scoliotic curve is the smallest angle between these two lines.

The Cobb method is the commonly used method to quantify scoliosis and consists of the following steps. First, the most tilted vertebrae at the top resp. the bottom of the curved segment are searched for. The surfaces of the upper resp. lower vertebral end plate tilt to the side of the curve to be measured. Second, a line tangent to the upper resp. lower vertebral end plate is drawn. Third, the angle between these tangent lines is the Cobb angle of scoliosis. For small angles yielding nearly parallel tangent lines, the intersection may lie outside the image, in which case intersecting perpendiculars are constructed, and the angle formed by these perpendiculars is the same Cobb angle of the curve.

Ferguson and Cobb angle have traditionally been performed by the radiologist by drawing lines on a film of the spine. In the Ferguson method, the basis entities to place are the midpoints of the appropriate vertebrae. In the Cobb method, the tangents to the most inclined vertebrae are to be drawn. When manually determining the tangent line, a point pair incident on the line may be used. However, the resulting geometric angle of the line is very sensitive to the exact location of each of the points, for the distance between these points is usually very small (w.r.t. the image dimension). Furthermore, the presence of a number imaging artefacts, impacting the image appearance, renders this task non-obvious and introduces substantial observer error when placing these entities. First, the vertebral image structure may be unclear due to the superposition of other anatomical content (burdening the identification of the vertebra midpoint). Second, borders of the vertebrae may be fuzzified due to perspective projection of the vertebral end plate surface onto the detector plane. Third, thick attenuating body parts like the shoulder girdle suffer from under-penetration. Fourth, grid lines of a metallic grid that aids in the full-spine stitching process, may cross the vertebra of interest. Finally, the presence of orthopaedic instruments may locally obscure the anatomic detail. A new measurement method for quantifying the scoliosis angles according to Cobb or Ferguson is introduced here, coping with these problems and using the registration methods outlined above.

When reporting the scoliosis angle, it is important to mention the method used and also which end vertebrae were chosen for the measurement. This latter data is especially important, since once chosen, the same levels should be used from then on to measure curvature on follow-up examinations.

In the lateral full-spine examination, certain amounts of cervical (neck) lordosis, thoracic (upper back) kyphosis and lumbar (lower back) lordosis are normally present. Deviations from this normal alignment may reflect abnormal kyphosis or lordosis or, more commonly, scoliosis.

In these applications, a number of sub-tasks can be distinguished: (a) identification of the most inclined vertebrae to locate the start and end of a curved spine segment; (b) labelling of these most inclined and the remaining vertebrae (both for insertion into the patient record and for further referral at future follow-up measurements); (c) selection of the vertebra's midpoint (to be used in the Ferguson method) or selection of a point pair on the endplate of most inclined vertebrae to determine the vertebra's body tangent line (to be used in the Cobb method). As stated, for the points in the latter point pair are generally very close to one another, a slight displacement of one of them may result in a large shift in the tangent line's angle, hence in the resulting value for the angle of Cobb.

As will become apparent from the sequel, these tasks are simultaneously solved by the use of the image superposition and registration methods as outlined in the computational strategy below. The principle is to register a model vertebra (with midpoint and label indicated) with an actual vertebra of which the position, orientation and scale is unknown. The model vertebra may either come from a reference image, or a reference database, or it may be the image area pertaining to the previous vertebra. After registration, the midpoint of the registered model determines the vertebra midpoint of the Ferguson method; the rotational component of the geometric transformation determines the angle of the registered model of the Cobb method. The basic notion is that the registration methods use all of the image area pertaining to the vertebral body (geometry component) and the grey value information contained in it (intensity component) to achieve the optimal registration; hence, the registration result is less sensitive to local grey value changes than methods that solely rely on isolated points and point features. Furthermore, they automate the problem of auto-location and auto-naming of the image structures of interest.

In the sequel, image A is the full-spine image onto which the scoliosis angles of Cobb or Ferguson are measured. The image information for image B may be chosen to be either (a) a reference full-spine image containing a non-scoliotic spine with all vertebrae labelled and oriented at zero degree, or a reference collection of smaller sized image Regions of Interest (ROI), each comprising the neighbourhood around a vertebra; or (b) a previous image of the full-spine of the same patient, called in for follow-up onto which or (c) the same image A, of which the previously registered vertebra stands model for the next vertebra. In either case, the image B constitutes an anatomic model for the spine for it comprises the ensemble of successive cervical, thoracic and lumbar vertebrae (C1 ... C7, T1 ... T12 and L1 ... L5).

Computational Strategy

Step 1.

Acquisition of a full-spine image, called image A.

Step 2.

Selection of a vertebra $V_i$ in image A, e.g by its midpoint, or by indicating its four corners. The quadrangle formed by the latter four corners approximately segments the vertebra. These geometric objects can be used to initialize the a rectangular or circular Region of Interest around the anatomic entity i.c. vertebra to be used in the subsequent alignment and registration.

Step 3.

Assignment of the anatomic label of the vertebra of image A of step 2, i.e. either one of the cervical vertebrae C1 ... C7, or one of the thoracic vertebrae T1 ... T12, or one of the lumbar vertebrae L1 ... L5. Step 2 and 3 may be combined in one step by selecting a pre-defined vertebra (e.g. vertebra L1, which is easily situated for it has no ribs attached).

Step 4.

Selection of the corresponding vertebra $V_i'$ in a previously acquired image, called image B. This selection step can be omitted if a reference image is used, or a database of ROI's of reference vertebrae. In that case, the corresponding vertebra can be looked up automatically for the label is known from step 3. This step also sets the initial parameters of the geometric transform.

Step 5. Registration of the vertebra $V_i'$ in image A with the vertebra $V_i'$ in image B according to the methods outlined above.

Step 6. Retrieving the actual position of the midpoint $M_i$ of the registered vertebra $V_i'$ of image B in the common coordinate system with image A; assigning the anatomic label of vertebra $V_i'$ to the vertebra $V_i$; assigning the final position at registration optimum of the anatomic ROI (e.g. rectangle) associated with vertebra $V_i'$ to the vertebra $V_i$. Store the items in a data record pertaining to the vertebra $V_i$.

Step 7. Extracting the rotational component $\alpha_i$ of the geometric transform that was finally applied to register the two vertebrae, and store it in a data record pertaining to the vertebra $V_i$.

Step 8. Moving upwards (or downwards) to the higher (lower) vertebra $V_{i-1}$ ($V_{i+1}$) or and re-iterate from step 4, until all vertebrae are identified, labelled and their midpoint and orientation recorded. The translation that is applied in the upward or downward movement is related to the height $h_i$ of vertebra $V_i$ and can be expressed as $(1-\alpha_i)h_i$ whereby the factor $\alpha_i$ is dependent on the label and rotation of $V_i$ (lumbar vertebrae requiring a larger translation than thoracic vertebrae). The number of iterations is determined by the number of vertebrae in the spinal model. It will typically cover a subset of the vertebrae C1 . . . C7, T1 . . . T12, L1 . . . L5.

Step 9a. Determination of the most inclined vertebrae $V_T$ resp. $V_B$ situated at the inflection points in the sequence of orientations of successive vertebrae. Denote the orientation of these top and bottom vertebrae $\alpha_T$ resp. $\alpha_B$.

Step 9b. Determination of the apex vertebra $V_A$ at the peak of the curve between $V_T$ and $V_B$. This apex vertebra is easily computed using principles of geometry applied to the sequence of successive midpoints. More specifically, the apex vertebra may be computed as the most deviated vertebra from a line connecting the inflection points of the curve segment.

Step 10. Calculation of the Ferguson angle $\alpha_{Ferguson}$ using the lines through the midpoints of $V_T$, $V_B$, and $V_A$.

Step 11. Calculation of the angle of Cobb $\alpha$ by subtracting the angles of the most inclined vertebrae, said angles expressed and compared in the common coordinate system, i.e. $\alpha_{Cobb} = \alpha_T - \alpha_B$.

A similar labelling strategy may be used on lateral full-spine images to label the vertebrae of the lateral view. Likewise, vertebral orientation is based on a global alignment of the vertebral body, to determine the angles of kyphosis of the thoracic trunk and lordosis of the lumbar trunk, between the appropriate vertebral levels of spinal inflection in the saggital plane.

Extension to 3D Images:

The principle of determining the segmental mobility of the cervical spine from the rotational component of the geometric transformation or for measuring angular difference between two vertebrae is extensible to 3D imagery. In both applications, the angular difference between the entities has three components of rotation, i.e. one around each of the x, y and z axis. The registration measure now operates on the voxel values instead of pixel values. The geometric transform of a rigid body motion includes three translational components in x,y and z direction, and three rotational components around the x, y and z axis of the coordinate system. The search strategy operates in the at least six-dimensional parameter space of the alignment parameters. In contrast to X-ray projection radiography, 3D imaging modalities do not superimpose organ and bone structure, hence the registration process can effectively be modeled by an Euclidean similarity transform.

The invention claimed is:

1. A method of computing the Ferguson angle in a spine image comprising
    for a curved segment of said spine image, determining the most inclined vertebrae at the inflection points in the sequence of orientations of successive vertebrae in said segment,
    for said curved segment, determining the apex vertebra at the peak of the curved segment between said most inclined vertebrae,
    determining the Ferguson angle as the angle between a first straight line through the center of the apex vertebra and the center of a first of said most inclined vertebrae and a second straight line through the center of the apex vertebra and the center of a second of said most inclined vertebrae, wherein said most inclined vertebrae are determined by evaluating rotation angles of vertebrae in said curved segment, and wherein said rotation angle of each vertebrae in said segment relative to a reference position in a reference image is determined by a method comprising the steps of:
    (1) obtaining a digital signal representation of an image of said segment;
    (2) obtaining a digital reference image B pertaining to a vertebrae in said segment and having the same dimension thereof;
    (3) applying the digital signal representation of the segment image to a display device coupled to a computer and displaying the segment image;
    (4) selecting a vertebrae in the displayed segment image;
    (5) computing parameters of a geometric transform comprising at least a rotational component and geometric transformation mapping said vertebrae from said reference image B onto the corresponding selected vertebrae in the segment image in a common coordinate system;
    (6) aligning said images by applying said geometric transform with the computed parameters to said reference image, wherein the rotational component of said transform determines the extent to which the position of said selected vertebrae in the segment is rotated, and obtaining the rotation angle for said selected vertebrae;
    (7) repeating steps (1)-(6) for each successive vertebrae in said segment.

2. The method according to claim 1, wherein the parameters are determined by:
    (1) computing initial parameters of said geometric transform;
    (2) aligning said images by applying said geometric transform with the computed parameters to said image of a vertebrae;
    (3) evaluating a cost function to generate a cost value indicating a degree of alignment;
    (4) updating parameters of said geometric transform taking into account said cost value; and
    (5) re-iterating steps (2) to (4) until an optimal cost value is found so as to obtain final parameters of a final transform.

* * * * *